United States Patent [19]

Komoda et al.

[11] Patent Number: 5,164,183

[45] Date of Patent: Nov. 17, 1992

[54] GROWTH PROMOTER FOR BIFIDOBACTERIUM SPECIES AND METHOD OF USING THE SAME

[75] Inventors: Akihiko Komoda, Saitama; Eiichi Katsunuma, Ashikaga; Minoru Uchida, Gunma, all of Japan

[73] Assignee: Tokyo Tanabe Company, Limited, Tokyo, Japan

[21] Appl. No.: 654,334

[22] Filed: Feb. 12, 1991

Related U.S. Application Data

[63] Continuation-in-part of Ser. No. 195,115, May 17, 1988, abandoned.

[30] Foreign Application Priority Data

May 22, 1987 [JP] Japan .................................. 61-123761

[51] Int. Cl.$^5$ ............................................. A61K 35/78
[52] U.S. Cl. ................................................. 424/195.1
[58] Field of Search ...................................... 424/195.1

[56] References Cited

U.S. PATENT DOCUMENTS 5,013,576 5/1991 Nakazawa et al. ................. 426/640

OTHER PUBLICATIONS

J.P.LO No. 219349, Feb. 1987, Abstract.
J.P.LO No. 96966, Sep. 1986, Watanabe et al., Ab.
J.P.LO No. 132868, Jul. 1984, Nakagawa, Ab.
J.P.LO No. 32458, Feb. 1988, Nakazawa et al. Ab.

*Primary Examiner*—John W. Rollins
*Attorney, Agent, or Firm*—McGlew & Tuttle

[57] ABSTRACT

A growth promoter for Bifidobacterium species comprising gourd food, from yugao gourd, as active ingredient is provided. The growth promoter has a more selective and more marked growth-promoting effect than conventional bifidus factors.

30 Claims, No Drawings

GROWTH PROMOTER FOR BIFIDOBACTERIUM SPECIES AND METHOD OF USING THE SAME

This is a continuation in part application of application Ser. No. 195,115 filed May 17, 1988, now abandoned.

BACKGROUND OF THE INVENTION (1) Field of the Invention

This invention relates to a growth promoter for Bifidobacterium species. More particularly, it relates to a growth promoter for Bifidobacterium species comprising gourd food of yugao gourd as the active ingredient, and a method of using such a growth promoter.

(2) Description of the Prior Art

Bacteria of the genus Bifidobacterium have no pathogenicity and occur principally in the intestine of man. It has been established that they have a physiological significance in the suppression of formation of intestinal putrefaction products and the improvement of diarrhea or constipation. Moreover, it has recently been reported that they enhance immunity, prevent the replacement of bacteria as encountered during continuous administration of antibiotics, and suppress the activity of carcinogens, and this has led to their wide applications in clinical fields ("Microorganisms", Vol. 1, No. 4, Igaku Shuppan Center). Thus, Bifidobacterium species are very important from the viewpoint of health and therapeutics.

There are two methods for growing Bifidobacterium species in the intestine. One of them is the direct method in which cells of Bifidobacterium species are administered orally, and the other is the indirect method in which a substance utilizable by Bifidobacterium species (hereinafter referred to as "bifidus factor") is administered to promote the growth of Bifidobacterium species. The direct method is disadvantageous in that the stability of Bifidobacterium preparations is poor and the degree of colonization of administered Bifidobacterium species is low. Accordingly, instead of the direct method, more importance has recently been attached to the indirect method in which a bifidus factor is orally administered to promote the growth of Bifidobacterium species in the intestine.

Conventionally, a variety of substances are known to act as bifidus factors. Specific examples thereof include N-acetylglucosamine and its derivatives, carrot extract (principally containing pantetheine), lactulose, raffinose, stachyose, maltotriose ("Bifidus Bacteria", Yakult Co., Ltd., 1979), fructooligosaccharide ("Kagaku-to-Seibutsu", Vol. 21, p. 291, 1983), galacto-oligosaccharide [U.S. Pat. No. 4,435,389 (U.K. Pat. 2,080,330; Japanese Patent Publication No. 20266/'83); Japanese Patent Publication No. 46479/'86; Japanese Patent Laid-Open No. 41449/'85], isomalto-oligosaccharide (a report presented at a meeting of the Japanese Society of Dietetics and Food Science, 1986), cyclodextrin [U.S. Pat. No. 4,451,457 (U.K. Pat. 2,092,890; Japanese Patent Laid-Open No. 138385/'82)], mannan from devil's tongue ("Riken Intestinal Flora Symposium III, Intestinal Flora and Nutrition", Gakkai Shuppan Center, p. 89, 1983), soybean milk (Japanese Patent Publication No. 9822/'70; Japanese Patent Laid-Open Nos. 142566/'76 and 85390/'80), soybean milk extract (Japanese Patent Laid-Open No. 179064/'84), an extract from a culture of non-pathogenic Escherichia species (Japanese Patent Publication No. 13359/'75), and the like.

The term "gourd" is a generic name for plants belonging to the family Cucurbitaceae, which family includes the genus Lagenaria and the genus Cucurbita.

The term "yugao" refers to bottle gourd or white flower gourd, an annual crawling plant of the family Cucurbitaceae whose botanical name is *Lagenaria siceraria Standl. var. hispida Hara* or *Lagenaria leucantha Rusby var. clavata Makino* (Illustrated Horticultural Flora In Colour, 1984, p. 440–445, Hokuryukan Co., Ltd., Tokyo, Japan; and Makino's Picture Book of Japanese Plants, Hokuryu-Kan, 1967 and 1969, p. 38–41).

The term "togan" or "kamouri" (both of which are synonymous) refers to wax gourd, an annual crawling plant of the family Cucurbitaceae whose botanical name is *Benincasa hispida* Cogn. or *Benincasa Certifera Savi*, and whose fruit, skin and seeds have long been used for their anti-inflammatory and diuretic activity.

For instance, the fruit of wax gourd may be dried and crushed, and then combined as is, or as its ethanol or water extract, with the spray dried steam extract of the soluble components of the leaf, stalk and other above ground parts to form a health tea (Japanese Patent Laid-Open No. 239875/'87). Also, the fruit of wax gourd may be sterilized, and after removing the seeds, extracted with aqueous solvent and the extract spray dried to form a powder combined with fermented tea leaves, i.e. *Thea Shinsesis*, and other ingredients to form an eye health tea for fatigued eyes caused by poor blood circulation or by hypoglycemia (Japanese Patent Laid-Open No. 56436/'87).

Yugao gourd (plant of the genus Lagenaria) is distinct from other gourds of the family Cucurbitaceae, such as togan (wax gourd), directly edible plants (U.S. Pat. No. 3,219,542 to Lammers) as exemplified by pumpkin, squash, cucumber and watermelon (Encyclopedia Americana, Intl. Ed. 1987, vol. 13, p. 125), and Buffalo gourd, a perennial plant of the genus Cucurbita whose botanical name is *Cucurbita foetidissimo* HBK (Chemical Abstracts, 84:149505k, 1986; and 93:235075n, 1980).

In Japan, yugao gourds have been eaten as food from olden times. Dried gourd shavings of yugao gourd are called "kanpyo" or "kampyo" (both of which are synonymous) and have long been used popularly as ingredients of sushi, plain dishes and the like. Yugao gourds are a highly nutritious food containing a well-balanced combination of sugars, fibers, protein, vitamins, calcium, pectin and the like. Moreover, it has recently been reported that gourd food lessens the influence of the human body of Amaranth (Red No. 2) used as a food dye, and has the effect of preventing the blood cholesterol level from rising (Annual Report on the Opening-up of New Markets and the Realization of Vision for the Year 1985, Tochigi Prefecture Gourd Trade Association).

Thus, there is an increasing demand for gourds as a healthful food ("My Health", Shufu-no-Tomo Co., May issue, 1986). Furthermore, yugao gourds are an important agricultural product in the whole area of Tochigi Prefecture, Japan, and it is eagerly desired to utilize them to the fullest extent.

However, it has not been known that gourd food made from yugao gourd promotes the growth of Bifidobacterium species.

Since dried gourd shavings of yugao gourd (kanpyo) have a water content of as high as 15 to 40% in themselves and, moreover, are a highly nutritious food, in time they tend to grow bacteria, mold and the like, and to turn brown in color. Thus, 3 or 4 months after preparation, they suffer an adverse change in properties (such as color, odor, taste, etc.) and quality. For this reason, much care has been required for storage thereof.

In order to keep the quality of dried gourd shavings, there has been proposed a method in which the flesh of a gourd is sliced into ribbons, dried and then fumigated with sulfur, e.g. as sulfurous acid or sulfur dioxide, for bleaching and sterilizing purposes [Japanese Patent Publication No. 21292/'82; "Food Industry", Vol. 3, Book II, p. 52 (1982)]. However, this method unavoidably causes the occurrence of residual sulfur. As sulfur is very harmful to human beings and the presence of any residual sulfur is undesirable, its presence in food is regulated (cf. the Food Sanitation Act of Japan). Thus, the sulfur fumigated and bleached dried gourd shavings must be washed in water prior to eating, which causes most of the water soluble nutrients (such as sugars, pectin, vitamins, etc.) therein to be washed away. Similarly, a gourd food made by reducing such dried shavings to powder is also deprived of most water soluble nutrients.

The sulfur fumigated and bleached kanpyo has to be well steeped in water, then boiled and thereafter washed extensively to remove residual sulfites. The gourd shavings turn brown upon being boiled, and up to about 60% of the nutrients, comprising almost 100% of the water soluble nutrients, are undesirably lost consequent the required sulfur constituent removal washing.

In one teaching, the fruit of yugao gourd that has been dehydrated, dried and pulverized to form a powdery product, is said to have the unique taste and flavor of gourd and high nutritive value for use with wheat flour or other raw material in making noodles, tofu (soybean curd), confectionary (cake), etc. (Japanese Patent Laid-Open No. 132868/'84). The dehydrating method is not indicated, but yugao gourd fruit (about 95% water content) is normally only dehydrated by press-squeezing the dried shavings (kanpyo) to express therefrom the 15 to 40% remaining moisture content, thus washing away the major nutrient content.

In a further teaching, the outer skin, including the attached pulp and core containing the seeds, is removed from initial or middle stage growth harvested yugao gourd, the obtained pulp is cut into small pieces and blanched by boiling for 10 minutes under undisclosed boiling conditions, the boiled pieces then frozen to induce partial disruption of the cell membranes and denature the tissue, followed by thawing at room temperature, dehydrating, drying and pulverizing of the pieces, for use as raw material for confectionary (cake) or as dietary fiber (Japanese Patent Laid-Open No. 96966/'86). Subjecting yugao gourd fruit flesh to this type of degrading treatment fosters formation of a three dimensional network structure that retains a large quantity of water and assumes a semi-gel form. This enables the degraded gourd pulverized product to increase the formability of confectionary or other food when included with the other ingredients in preparing the food.

However, blanching or boiling of yugao gourd fruit causes major loss of its water soluble nutrients and edible fibers, and further loss thereof occurs upon dehydrating yugao gourd fruit, which is normally only effected by press-squeezing the dried shavings to express the retained moisture content therefrom.

In a still further teaching, commercial dried gourd shavings (kanpyo) are boiled in water or steeped and then steamed, to form an instant food for use in cooking upon regeneration with hot water (Japanese Patent Laid-Open No. 219349/'87). The boiling or steeping and steaming, serves to remove sulfur residue consequent earlier sulfur fumigating and bleaching of yugao gourd dried shavings (kanpyo) in preparing the commercial gourd shavings. Hence, the water soluble components in the dried gourd shavings, i.e. the nutrient components, including sugars, vitamins, amino acids and minerals, and edible fibers, are washed away.

In order to overcome the above described disadvantages, there has been proposed a gourd food of yugao gourd (unbleached dried gourd) made without bleaching by fumigation with sulfur. This gourd food is quite safe from the viewpoint of food sanitation, is highly nutritious, and has good keeping quality, so that it can be eaten for nourishing purposes, i.e. as a food itself, as is, in normal nourishing or hunger satisfying quantities or bulk amounts (Japanese Patent Laid-Open No. 32458/'88). The underlying objective of this teaching is to combine the unbleached dried gourd, as is, with another food to impart the taste and modifying characteristics of the other food thereto in view of the peculiar grassy smell, characteristic bitter strong taste, stickiness property, etc. of the yugao gourd from which it is made, thereby making the gourd itself easier to eat. The optimal amounts used are selected to provide the unbleached dried gourd in a nourishing amount with the other food.

It is also known that unbleached dried gourd (yugao) has a neutral detergent fiber (NDF) content of about 30% (Japanese Patent Laid-Open No. 32458/'88). NDF is a typical food fiber, and it is well known that people taking plenty of food fibers have a low incidence of rectal cancer.

The above-described conventional bifidus factors have the disadvantage that, in the living body, they are also utilized by other intestinal bacteria such as lactic acid bacteria and are not sufficiently effective in promoting the growth of Bifidobacterium species. Moreover, the processes for preparing these bifidus factors are tedious and/or they are expensive. Accordingly, it is desired to develop a bifidus factor which is selectively utilized by Bifidobacterium species in the living body and can effectively promote the growth thereof. Moreover, if such a bifidus factor is cheap and easy to obtain or prepare, its utility will become still greater.

SUMMARY OF THE INVENTION

The present inventors have made a study of bifidus factors and have found that gourd food, made from yugao gourd, and known from olden times, can selectively and markedly promote the growth of Bifidobacterium species. The present invention has been completed on the basis of this finding.

According to the present invention, there are provided a growth promoter for Bifidobacterium species comprising gourd food as the active ingredient, and a method of using such a growth promoter. This gourd food is in the form of dried gourd food such as unbleached dried gourd food (yugao).

The term "dried gourd" as used according to the present invention means yugao gourd (bottle gourd or white flower gourd) of the botanical name *Lagenaria siceraria Standl.* var. *hispida Hara* or *Lagenaria leucantha Rusby* var. *clavata Makino*, that has been dried until it has a water content of not greater than 8% by weight, and the term "unbleached dried gourd" is the same yugao gourd that has not been bleached by sulfur fumigation, but which has been sterilized and dried, e.g.

steam sterilized and hot air dried, until it has a water content of not greater than 8% by weight. This dried gourd or unbleached dried gourd, made from yugao gourd, comprises the dried gourd food of the present invention, which is suitably in powder or other particle form.

The various features of novelty which characterize the invention are pointed out with particularity in the claims annexed to and forming a part of this disclosure. For a better understanding of the invention, its operating advantages and specific objects attained by its uses, reference is made to the accompanying descriptive matter in which preferred embodiments of the invention are illustrated.

DETAILED DESCRIPTION OF THE PREFERRED EMBODIMENTS

The growth promoter for Bifidobacterium species in accordance with the present invention comprises gourd food, made from yugao gourd, as the active ingredient. The term "gourd food" as used herein comprehends various products obtained by processing yugao gourds into desired forms including strips, powder, granules, tablets and the like. The gourd food is prepared by peeling off the rind of the yugao gourd and slicing the flesh thereof to obtain gourd shavings. The obtained gourd shavings are dried until they have a water content of not greater than 8%, especially not greater than about 3%, preferably after being exposed to sunlight for about a day, to form the gourd food.

The gourd food may be sterilized by exposing the dried gourd shavings to steam at a pressure of 0.2 to 0.4 kg/cm$^2$ for a period of 5 to 20 minutes, or by adding ethyl alcohol or isopropyl alcohol to such shavings in an amount of 15 to 150 g/kg (dried gourd) and allowing it to stand for a period of 1 to 30 days (Japanese Patent Laid-Open No. 32458/'88). This sterilized gourd food has a standard plate count of not greater than $5 \times 10^3$ cells/g of gourd food, is negative to the tests for the coliform group and Salmonella species, and is dried to have a water content of not greater than 8%, especially not greater than about 3%. Thus, it is quite safe from a food sanitation viewpoint.

As the gourd food of the present invention may be produced by the above described sterilization methods, it does not cause inhabitation or infestation of fungi (molds) or pests, and the nutrients remain as they are in the original yugao gourd. Unlike sulfur fumigated and bleached kanpyo, which must be boiled and washed before eating, the yugao gourd food of the present invention can be eaten as is. The sterilizing procedure is part of the set of steps for producing the preferred gourd food of the present invention. Only through this procedure is gourd food obtained, which is not susceptible to fungi (molds) and pest inhabitation or infestation, yet which retains the original nutrients. It differs from sulfur fumigated and bleached kanpyo in terms of its sanitary and nutrient condition, and its physiological activity in promoting growth of Bifidobacterium species.

The typical amounts of retained original nutrient components in the dried gourd food of the present invention are as follows:

| Components | |
| --- | --- |
| water | 1.1% |
| protein | 8.6% |
| lipids | 0.8% |
| fibers | 10.9% |
| ash content | 5.7% |
| sugars | 72.9% |
| energy | 327 kcal/100 g |
| phosphorus | 257 mg/100 g |
| iron | 7.07 mg/100 g |
| calcium | 393 mg/100 g |
| sodium | 3.00 mg/100 g |
| potassium | 2.14% |
| total pectins | 6.61% |
| edible fibers | 34.2% |
| water soluble content | hardly any |
| digestible polysaccharides | 3.86% |
| hemicellulose | 15.8% |
| cellulose | 14.2% |
| lignin | 0.37% |

Unlike the high loss of nourishing ingredients resulting from the aforesaid washing of the kanpyo dehydrated, dried and powdered product (Japanese Patent Laid-Open No. 132868/'84), the sterilized unbleached dried gourd food of the present invention only loses 36.5% of its edible fiber content (compared to 87.5%), 11.9% of its cellulose content (compared to 35.7%), 2.9% of its hemicellulose content (compared to 5.5%), 2.0% of its lignin content (compared to 2.4%) and 8.0% of its pectin content (compared to 13.1%).

The Bifidobacterium growth promoting constituents in the dried gourd food (yugao) herein are advantageously retained and usable in suitable therapeutic dosages, because it is not subjected to washing away of its nutrients, including its natural Bifidobacterium growth promoting constituents, as in the case of sulfur fumigated and dried gourd, or dehydrated and dried gourd.

Although the growth promoter of the present invention may comprise the gourd food alone, it can further contain various additives. When used with one or more such additives, the dried gourd food, e.g. shavings or strips, are reduced to a powder, combined with the additive or additives, and formed into a composition of particles such as powder, granules or tablets.

Such additives include, for example, fibrous components such as sweet corn, carrot powder, corn fiber, apple fiber, pumpkin powder, alginic acid, etc.; excipients such as lactose, starch, etc.; sweetenings or sweeteners such as white sugar, malt sugar, sorbitol, mannitol, etc.; nutriments such as milk powder, meat extract, etc.; binders such as gum arabic powder, polyvinyl pyrrolidone, hydroxypropylcellulose, carboxymethylcellulose sodium, etc.; and lubricants such as magnesium stearate, calcium stearate, Lubri Wax (trademark), i.e. hydrogenated caster oil, talc, etc. These additives may suitably be chosen and used according to the form of the gourd food and/or the taste.

Where the gourd food constituting the active ingredient of the growth promoter of the present invention is used alone, it may be eaten in appropriate dosage as such or after being cooked. Alternatively, it may be formed into powder, granules or tablets and used in appropriate dosage in any of these particle forms.

The gourd food of the present invention is derived from a natural plant and has not been shown to have any toxicity to human beings. For proliferating Bifidobacterium species, it may be used in a suitable individual therapeutic dosage of about 1 to 10 g (e.g. per meal), and in a total daily therapeutic dosage of about 3 to 30 g. Desirably, the gourd food has a standard plate count not greater than 5×10³ cells/g gourd food, tests negative to the coliform group and Salmonella species, and has a water content not greater than 8%, especially not greater than 3%.

The present invention contemplates a growth promoter composition for Bifidobacterium species comprising a Bifidobacterium species growth promoting dosage amount of dried gourd food having a water content of not greater than 8%, from yugao gourd, as active ingredient and a food additive therefor, such as a fibrous component, excipient, sweetener, nutriment, binder or lubricant, in an amount of about 1 to 10%, based on the total weight of the composition, the composition being in particle form, such as powder, granule or tablet form. Preferably, the composition comprises a dosage having a dosage weight of about 0.1 to 11 g as tablets, and especially about 1.01 to 11 g, including about 1 to 10 g of dried gourd food and about 0.01 to 1 g of food additive, in powder, granule or tablet form.

The present invention also contemplates a method of using gourd food for promoting the growth of Bifidobacterium species in the human body, comprising administering orally a Bifidobacterium species growth promoting dosage amount of dried gourd food having a water content of not greater than 8%, from yugao gourd. When used alone, it is administered in a daily therapeutic dosage of about 3 to 30 g, and when used in the composition with the food additive, it is administered in a daily therapeutic dosage of about 3.03 to 33 g, including about 3 to 30 g of the dried gourd food and 0.03 to 3 g of the food additive.

Hence, the therapeutic dosage amount of the gourd food used according to the present invention is selected on a basis having nothing to do with the amount of gourd food, such as unbleached dried gourd food, normally used to provide a nourishing amount thereof, as is, or together with another food.

Preferred examples of the invention are described hereinafter by way of illustration and not limitation.

The growth-promoting effect of the gourd food of the present invention on Bifidobacterium species will be more specifically explained with reference to the following tests.

The gourd food samples used in these tests were gourd powder (Example 1), gourd granules (Example 2) and sterilized gourd powder, i.e. "unbleached dried gourd", from yugao gourd (Example 4). None of the gourd food in these tests, or in the Examples that follow, was made from yugao gourd that had been subjected to bleaching by sulfur fumigation treatment.

TEST 1

Negishi's agar medium (Journal of the Japanese Bacteriological Society, Vol. 13, p. 519, 1958) was used as a basal medium for the testing of bifidus factors. Each of various bifidus factors was added thereto in an amount of 0.5%. Each of the resulting media was placed in a Petri dish of 9 cm diameter and inoculated with *Bifidobacterium longum* (ATCC 15707) at a density of about 50 cells per plate. This dish was incubated at 37° C. for 48 hours and then observed for the degree of growth of the bacterium. The results thus obtained are shown in Table 1.

TABLE 1

| Test sample (bifidus factor) | Degree of growth |
| --- | --- |
| None (basal medium alone) | + |
| Gourd powder (Example 1) | + + + + |

TABLE 1-continued

| Test sample (bifidus factor) | Degree of growth |
| --- | --- |
| Sterilized gourd powder (Example 4) | + + + + |
| Isomalto-oligosaccharide | + + + |
| Fructo-oligosaccharide | + + + |
| Glucose | + + |
| Lactose | + + |
| Cellulose | + + |
| Pectin | + + |

+ + + +: Marked degree of growth.
+ ~ + + +: Appreciable degrees of growth.

As is evident from Table 1, the gourd powder and the sterilized gourd powder promoted the growth of Bifidobacterium species unexpectedly more markedly than the conventional bifidus factors. At a 0.5% concentration, each of these gourd powders was four times as effective as the control (basal medium alone), compared to two or three times such effect for the conventional bifidus factors.

TEST 2

To Tomarelli's medium (J. Biol. Chem., 181, 879, 1949) used as a basal medium, gourd powder (Example 1) was added in various amounts ranging from 0 to 2%. Each of the resulting media was inoculated with *Bifidobacterium longum* (ATCC 15707), *Lactobacillus plantarum* (ATCC 8014) or *Escherichia coli* (ATCC 11775) and incubated at 37° C. for 48 hours. After completion of the incubation, the cultures of *Bifidobacterium longum*, *Lactobacillus plantarum* and *Escherichia coli* were spread over BL agar medium, LBS agar medium and EMB agar medium, respectively. After these media were incubated at 37° C. for 48 hours, the bacterial count of each medium was made. The results thus obtained are shown in Table 2.

TABLE 2

| Amount of gourd powder added (%) | Bacterial count (cells/ml) | | |
| --- | --- | --- | --- |
| | Bifidobacterium Longum | Lactobacillus plantarum | Escherichia coli |
| 0 (not added) | 2.0 × 10⁵ | 3.8 × 10⁸ | 1.3 × 10⁸ |
| 0.05 | 2.0 × 10⁶ | 5.0 × 10⁸ | 7.4 × 10⁷ |
| 0.1 | 1.0 × 10⁸ | 7.1 × 10⁸ | 6.4 × 10⁷ |
| 0.2 | 1.1 × 10⁸ | 6.7 × 10⁸ | 5.9 × 10⁷ |
| 0.5 | 5.4 × 10⁸ | 5.0 × 10⁸ | 1.3 × 10⁷ |
| 1.0 | 6.9 × 10⁸ | 3.7 × 10⁸ | 1.6 × 10⁷ |
| 2.0 | 5.9 × 10⁸ | 4.2 × 10⁸ | 2.1 × 10⁷ |

As is evident from Table 2, the gourd powder promoted the growth of *Bifidobacterium longum* by a factor of 10 at a concentration of 0.05% and by a factor of about 1,000 at a concentration of 0.1 to 2.0%, compared to the control (basal medium alone). In contrast, it was scarcely utilized by *Lactobacillus plantarum* and *Escherichia coli*.

TEST 3

Gourd granules (Example 2), sterilized gourd powder (Example 4) and conventional bifidus factors were used as samples.

Each of the samples was added to Tomarelli's medium. The resulting media were incubated with *Bifidobacterium longum* (ATCC 15707) and incubated at 37° C. for 48 hours. After completion of the incubation, each of the cultures was spread over BL agar medium and incubated at 37° C. for 48 hours. Thereafter, a bacterial count was made. The results thus obtained are shown in Table 3.

TABLE 3

| Sample | Concentration (%) | Bacterial count of Bifidobacterium longum (cells/ml) |
|---|---|---|
| None (control) | — | $2.0 \times 10^4$ |
| Gourd granules (Example 2) | 0.1 | $2.0 \times 10^6$ |
| | 0.5 | $1.2 \times 10^8$ |
| | 1.0 | $4.8 \times 10^8$ |
| Sterilized gourd powder (Example 4) | 0.1 | $1.0 \times 10^6$ |
| | 0.5 | $5.4 \times 10^8$ |
| | 1.0 | $3.9 \times 10^8$ |
| Fructo-oligo-saccharide | 0.1 | $1.5 \times 10^4$ |
| | 0.5 | $4.4 \times 10^6$ |
| | 1.0 | $8.7 \times 10^6$ |
| Isomalto-oligo-saccharide | 0.1 | $7.8 \times 10^4$ |
| | 0.5 | $3.0 \times 10^6$ |
| | 1.0 | $5.9 \times 10^6$ |
| Pectin | 0.1 | $2.3 \times 10^5$ |
| | 0.5 | $6.6 \times 10^6$ |
| | 1.0 | $7.9 \times 10^6$ |

As is evident from Table 3, the gourd granules containing an additive and the sterilized gourd powder promoted the growth of Bifidobacterium species unexpectedly more markedly than the conventional bifidus factors.

Each of the gourd granules and gourd powder was more effective by a factor of about 100 at a concentration of 0.1%, and by a factor of about 10,000 at a concentration of 0.5 to 1.0%, compared to the control (basal medium alone). In contrast, each of fructo-oligosaccharide and isomalto-oligosaccharide was of about the same effect as the control at a concentration of 0.5%, and only more effective by a factor of about 100 at a concentration of 0.1 to 1.0%, compared to the control, while pectin was only more effective than the control by a factor of about 10 at a concentration of 0.1%, and by a factor of about 100 at a concentration of 0.5 to 1.0%.

TEST 4

To five healthy adult subjects, a daily dose of 2 g of gourd powder (Example 1) was administered before meals for 7 days. Similarly, a daily dose of 4 g of gourd granules (Example 2) was administered before meals for 7 days. In either case, the feces of each subjected were collected on day 7 and cultured. Thus, Bifidobacterium species growing on BL medium, as well as Lactobacillus species and coliform group, were counted and the respective average values were calculated. The results thus obtained are shown in Table 4.

TABLE 4

| | | Bacterial count (cells/g of feces) | | |
|---|---|---|---|---|
| | | Bifidobacterium species | Lactobacillus species | coliform group |
| Gourd powder | Before administration | $1.5 \times 10^9$ | $1.2 \times 10^5$ | $4.7 \times 10^6$ |
| | After administration | $1.6 \times 10^{10}$ | $2.5 \times 10^5$ | $5.9 \times 10^6$ |
| Gourd granules | Before administration | $9.0 \times 10^8$ | $2.2 \times 10^5$ | $6.3 \times 10^6$ |
| | After administration | $5.3 \times 10^9$ | $3.8 \times 10^5$ | $5.6 \times 10^6$ |

As is evident from Table 4, the gourd powder and the gourd granules selectively and unexpectedly markedly promoted the growth of Bifidobacterium species in the intestine of man.

EXAMPLE 1

The rind of a yugao gourd (bottle gourd or white flower gourd) was peeled off, and its flesh was sliced to obtain gourd shavings. These gourd shavings were exposed to the sun for a day and then dried at 70° C. for 5 hours. Thus, gourd food, made from yugao gourd, having a water content of about 3% was obtained in the form of strips. Using a pulverizer (manufactured by Hosokawa Tekkosho), 30 kg of the strips were pulverized to obtain 24 kg of gourd powder.

EXAMPLE 2

Using a stirring mixer, 950 g of the gourd powder obtained in Example 1 and 40 g of hydroxypropylcellulose as binder were mixed for 10 minutes. After the addition of purified water, the mixture was kneaded and then dried in hot air. After the resulting product was allowed to cool, its particle size was adjusted by means of an oscillator (manufactured by Kikusui Seisakusho) to obtain 960 g of gourd granules (containing by weight about 96% of the gourd powder and 4% of the binder).

EXAMPLE 3

Using a stirring mixer, 495 g of the gourd granules obtained in Example 2 and 5 g of magnesium stearate as lubricant were mixed for 10 minutes. Then, using a tableting machine, this mixture was formed into tablets. Thus, there were obtained 4,400 tablets of gourd food each having a weight of 110 mg or 0.11 g (containing by weight about 95.2% of the gourd powder, 3.8% of the hydroxypropylcellulose and 1.0% of the magnesium stearate).

EXAMPLE 4

30 kg of gourd shavings obtained in the same manner as described in Example 1 were sterilized by exposure to steam at a pressure of 0.2 kg/cm² for 20 minutes, and then dried in hot air at 60° C. until a water content of about 3% was attained. Thereafter, the same procedure as described in Example 1 was repeated to obtain 26 kg of sterilized gourd powder (i.e. "unbleached dried gourd" in powder form, made from yugao gourd).

This gourd powder had a standard plate count of $2 \times 10^2$ cells/g and was negative to the tests for the coliform group and Salmonella species.

EXAMPLE 5

30 kg of gourd shavings obtained in the same manner as described in Example 1 were sterilized by spraying them with ethyl alcohol in an amount of 2.7 kg (90 g/kg of gourd shavings) and allowing them to stand in a sealed condition at room temperature for 5 days. Thereafter, the same procedure as described in Example 1 was repeated to obtain 25.7 kg of sterilized gourd powder.

This gourd powder had a standard plate count of 37 cells/g and was negative to the tests for the coliform group and Salmonella species.

As described above, the growth promoter for Bifidobacterium species in accordance with the present invention comprises gourd food as the active ingredient, i.e. dried gourd food having a water content of not greater than 8%, made from yugao gourd, that is not subjected to bleaching by sulfur fumigation, and that unexpectedly has a more selective and more marked growth-promoting effect than conventional bifidus factors. Thus, this growth promoter for Bifidobacterium species not only serves to maintain the health of the gastrointestinal tract, but also can be expected to be useful as an immunoactivator, anticancer agent and other drugs. Moreover, since yugao gourds are being produced in large amounts in Japan, the present invention contributes to the development of the agricultural industry and also has great utility in the food industry and in therapeutics.

While specific embodiments of the invention have been shown and described in detail to illustrate the application of the principles of the invention, it will be understood that the invention may be embodied otherwise without departing such principles.

What is claimed is:

1. Growth promoter composition for Bifidobacterium species comprising a Bifidobacterium species growth promoting dosage amount of dried gourd food having a water content of not greater than 8%, from yugao gourd, as active ingredient and a food additive therefor in an amount of about 1–10%, based on the total weight of the composition, the composition being in orally administrable particle form.

2. Composition of claim 1 having a dosage weight of up to about 11 g.

3. Composition of claim 1 wherein the gourd food has a standard plate count of not greater than $5 \times 10^3$ cells/g of gourd food, and tests negative to the coliform group and Salmonella species.

4. Composition of claim 1 wherein the food additive is a fibrous component, excipient, sweetener, nutriment, binder or lubricant.

5. Growth promoter composition for Bifidobacterium species comprising a Bifidobacterium species growth promoting dosage amount of dried gourd food having a water content of not greater than 8%, from yugao gourd, as active ingredient and a food additive therefor in an amount of about 1–10%, based on the total weight of the composition, the composition being in orally administrable powder form.

6. Composition of claim 5 having a dosage weight of up to about 11 g.

7. Composition of claim 5 wherein the gourd food has a standard plate count of not greater than $5 \times 10^3$ cells/g of gourd food, and tests negative to the coliform group and Salmonella species.

8. Composition of claim 5 wherein the food additive is a fibrous component, excipient, sweetener, nutriment, binder or lubricant.

9. Growth promoter composition for Bifidobacterium species comprising a Bifidobacterium species growth promoting dosage amount of dried gourd food having a water content of not greater than 8%, from yugao gourd, as active ingredient and a food additive therefor in an amount of about 1–10%, based on the total weight of the composition, the composition being in orally administrable granule form.

10. Composition of claim 9 having a dosage weight of up to about 11 g.

11. Composition of claim 9 wherein the gourd food has a standard plate count of not greater than $5 \times 10^3$ cells/g of gourd food, and tests negative to the coliform group and Salmonella species.

12. Composition of claim 9 wherein the food additive is a fibrous component, excipient, sweetener, nutriment, binder or lubricant.

13. Composition of claim 9 wherein the food additive is a binder.

14. Growth promoter composition for Bifidobacterium species comprising a Bifidobacterium species growth promoting dosage amount of dried gourd food having a water content of not greater than 8%, from yugao gourd, as active ingredient and a food additive therefor in an amount of about 1–10%, based on the total weight of the composition, the composition being in orally administrable tablet form.

15. Composition of claim 14 wherein the tablet has a dosage weight of up to about 11 g.

16. Composition of claim 14 wherein the gourd food has a standard plate count of not greater than $5 \times 10^3$ cells/g of gourd food, and tests negative to the coliform group and Salmonella species.

17. Composition of claim 14 wherein the food additive is a fibrous component, excipient, sweetener, nutriment, binder or lubricant.

18. Composition of claim 14 wherein the food additive comprises a binder and a lubricant.

19. Growth promoter composition for Bifidobacterium species comprising a Bifidobacterium species growth promoting dosage amount of dried gourd food having a water content of not greater than 8%, from yugao gourd, that has not been bleached by sulfur fumigation, as active ingredient and a fibrous component, excipient, sweetener, nutriment, binder or lubricant as a food additive therefor in an amount of about 1–10%, based on the total weight of the composition, the composition being in orally administrable particle form and comprising a dosage having a dosage weight of about 0.1–11 g.

20. Method of using gourd food for promoting the growth of Bifidobacterium species in the human body, comprising administering orally a Bifidobacterium species growth promoting dosage amount of dried gourd food having a water content of not greater than 8%, made from yugao gourd.

21. Method of claim 20 wherein the gourd food is administered in a daily dosage of about 3–30 g.

22. Method of claim 20 wherein the gourd food has a standard plate count of not greater than $5 \times 10^3$ cells/g of gourd food, and tests negative to the coliform group and Salmonella species.

23. Method of claim 20 wherein the gourd food is in the form of a composition with a food additive therefor in an amount of about 1–10%, based on the total weight of the composition, the composition being in orally administrable particle form.

24. Method of claim 23 wherein the composition is administered in a daily dosage of about 3.03–33 g.

25. Method of claim 23 wherein the food additive is a fibrous component, excipient, sweetener, nutriment, binder or lubricant.

26. Method of claim 23 wherein the dried gourd food is unbleached dried gourd food that has not been bleached by sulfur fumigation.

27. Method of claim 23 wherein the composition is in tablet form.

28. Method of claim 27 wherein the composition is administered in a daily dosage of about 3.03–33 g.

29. Method of claim 27 wherein the food additive is a fibrous component, excipient, sweetener, nutriment, binder or lubricant.

30. Method of claim 27 wherein the dried gourd food is unbleached dried gourd food that has not been bleached by sulfur fumigation.

* * * * *